United States Patent
Behler et al.

(10) Patent No.: US 9,790,172 B2
(45) Date of Patent: *Oct. 17, 2017

(54) SULFATED OLIGOHYDROXYCARBOXYLIC ACID ESTERS, AND USE THEREOF

(71) Applicant: BASF SE, Ludwigshafen (DE)

(72) Inventors: Ansgar Behler, Bottrop (DE); Frank Clasen, Hilden (DE)

(73) Assignee: BASF SE, Ludwigshafen (DE)

( * ) Notice: Subject to any disclaimer, the term of this patent is extended or adjusted under 35 U.S.C. 154(b) by 39 days.

This patent is subject to a terminal disclaimer.

(21) Appl. No.: 14/895,679

(22) PCT Filed: May 28, 2014

(86) PCT No.: PCT/EP2014/061086
§ 371 (c)(1),
(2) Date: Dec. 3, 2015

(87) PCT Pub. No.: WO2014/195210
PCT Pub. Date: Dec. 11, 2014

(65) Prior Publication Data
US 2016/0102050 A1 Apr. 14, 2016

(30) Foreign Application Priority Data

Jun. 3, 2013 (EP) .................... 13170255

(51) Int. Cl.
| | |
|---|---|
| C07C 303/24 | (2006.01) |
| C07C 309/17 | (2006.01) |
| C07C 305/06 | (2006.01) |
| C11D 1/16 | (2006.01) |
| C07C 305/04 | (2006.01) |
| A61K 8/46 | (2006.01) |
| A61K 47/20 | (2006.01) |
| A61Q 5/02 | (2006.01) |
| A61Q 9/02 | (2006.01) |
| A61Q 19/00 | (2006.01) |
| A61Q 19/10 | (2006.01) |
| C07C 67/03 | (2006.01) |
| C07C 303/18 | (2006.01) |
| C11D 1/28 | (2006.01) |

(52) U.S. Cl.
CPC ............ *C07C 309/17* (2013.01); *A61K 8/466* (2013.01); *A61K 47/20* (2013.01); *A61Q 5/02* (2013.01); *A61Q 9/02* (2013.01); *A61Q 19/007* (2013.01); *A61Q 19/10* (2013.01); *C07C 67/03* (2013.01); *C07C 303/18* (2013.01); *C07C 303/24* (2013.01); *C07C 305/04* (2013.01); *C07C 305/06* (2013.01); *C11D 1/16* (2013.01); *C11D 1/28* (2013.01); *A61K 2800/28* (2013.01)

(58) Field of Classification Search
None
See application file for complete search history.

(56) References Cited

FOREIGN PATENT DOCUMENTS

| | | | |
|---|---|---|---|
| DE | 4003096 | 8/1991 | |
| DE | 4340042 | 6/1995 | |
| EP | 0530866 | 3/1993 | |
| GB | EP 0530866 A1 * | 3/1993 | ........... C07C 305/06 |
| WO | WO-2014/195208 | 12/2014 | |

OTHER PUBLICATIONS

PCT Written Opinion in PCT/EP2014/061086, Dec. 3, 2015, 5 pages.
English translation of International Search Report in PCT/EP2014/061086, mailed Jul. 31, 2014, 2 pgs.

* cited by examiner

*Primary Examiner* — Robert A Wax
*Assistant Examiner* — Melissa Mercier
(74) *Attorney, Agent, or Firm* — Marshall, Gerstein & Borun LLP

(57) ABSTRACT

Sulfated oligohydroxycarboxylic acid esters have the general formula (I):

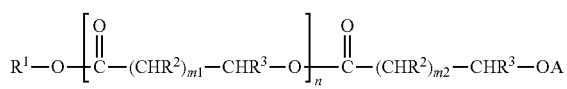

wherein at least one of the radicals A is —SO$_3$B. Cosmetic and pharmaceutical agents contain said esters. These esters are effective as anionic surfactants.

18 Claims, No Drawings

SULFATED OLIGOHYDROXYCARBOXYLIC ACID ESTERS, AND USE THEREOF

CROSS-REFERENCE TO RELATED APPLICATIONS

This application is the National Stage entry of PCT/EP2014/061086, filed on May 28, 2014, which claims priority to European Application Number 13170255.7, filed on Jun. 3, 2013, which is incorporated herein by reference in their entireties.

BACKGROUND OF THE INVENTION

The present invention relates to sulfated esters of oligohydroxycarboxylic acids, to cosmetic and pharmaceutical compositions which comprise these esters, and to the use of these esters as anionic surfactants.

PRIOR ART

Anionic surfactants belong to the most widespread interface-active compounds and, apart from being used in detergents and cleaners, are also used widely in the field of cosmetics. Customary anionic surfactants as are used primarily in cosmetics are the salts of alkyl ether sulfates (alkyl polyether sulfates, fatty alcohol polyglycol ether sulfates, also abbreviated to ether sulfates). They are characterized by strong foaming capacity, high cleaning strength, low curing and fat sensitivity and are often used for producing cosmetic products such as, for example, hair shampoos, foam or shower baths, but also in manual dishwashing detergents.

For many current applications, further requirements are placed on anionic surfactants apart from a good interface-active effect. Particularly in cosmetics, high dermatological compatibility is required. Furthermore, as a rule adequate solubility in water, good compatibility with as many as possible of the active ingredients and auxiliaries used in cosmetics, a good foam forming capacity and good rheological behavior is desired. Furthermore, there is a need for anionic surfactants which can be produced at least in part from biogenic sources and specifically also renewable raw materials. Furthermore, there is also a need for surfactants which have no alkoxylated groups and which therefore render superfluous the use of ethylene oxide in particular for their preparation.

EP 0 530 866 A1 describes sulfated esters of alkanecarboxylic acids and their use as surface-active compounds which, upon skin contact, are hydrolyzed and release an active component (e.g. a hydroxycarboxylic acid ester).

DE 40 03 096 A1 describe sulfated hydroxycarboxylic acid esters and their use as surface-active substances. Example A, described on page 4 of this document, for preparing lauryl lactate is not practicable technical teaching for preparing lauryl esters of lactic acid oligomers. For example, it is not even possible to heat to the stated 225° C. the esterification using toluene as entrainer, which forms an azeotrope with a boiling point of about 80 to 90° C. with the water that is liberated during the reaction, using a water separator.

DE 43 40 042 A1 describes the use of sulfate surfactants as described in DE 40 03 096 A1 as surface-active substances in cleaning and rinsing compositions for the cleaning and rinsing of hard surfaces.

The object of the present invention is to provide novel compounds which are advantageously suitable as interface-active compounds for various applications. Specifically, they should be suitable for covering a complex spectrum of requirements, as described at the start. In particular, it should be possible to provide surfactant-containing formulations which have application properties that are at least comparable with anionic surfactants based on petrochemical components and/or based on alkylene oxides known from the prior art.

Surprisingly, it has now been found that this object is achieved by sulfated esters of oligohydroxycarboxylic acids.

SUMMARY OF THE INVENTION

The invention firstly provides compounds of the general formula (I)

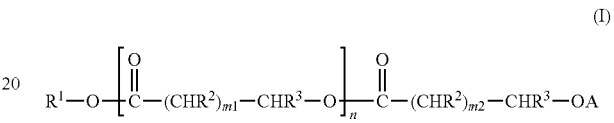

in which
R$^1$ is hydrogen or a linear or branched aliphatic hydrocarbon radical having 1 to 30 carbon atoms and 0, 1, 2 or 3 double bonds,
the radicals R$^2$, independently of one another, are selected from hydrogen, methyl, ethyl, —OA, —COOR$^4$, —CH$_2$—OA and —CH$_2$—COOR$^4$, where the radicals R$^4$ are hydrogen or a linear or branched aliphatic hydrocarbon radical having 1 to 30 carbon atoms and 0, 1, 2 or 3 double bonds,
the radicals R$^3$, independently of one another, are selected from hydrogen, methyl, ethyl, —OA, —COOR$^5$, —CH$_2$—OA and —CH$_2$—COOR$^5$, where the radicals R$^5$ are hydrogen or a linear or branched aliphatic hydrocarbon radical having 1 to 30 carbon atoms and 0, 1, 2 or 3 double bonds,
A is H or —SO$_3$B, in which B is hydrogen or a cation equivalent,
n is on average a value of at least 0.1,
m1 and m2, independently of one another, are 0 or 1,
with the proviso that at least one of the radicals A is —SO$_3$B, and
with the proviso that at least one of the radicals R$^1$, R$^4$ or R$^5$ is a linear or branched aliphatic hydrocarbon radical having 1 to 30 carbon atoms and 0, 1, 2 or 3 double bonds.

Sulfated esters of oligolactates are a preferred embodiment. Accordingly, the compounds of the general formula (I) are selected from compounds of the formula (I.1)

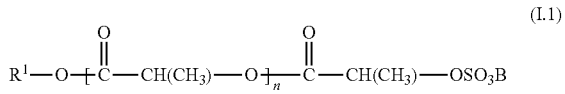

in which
R$^1$ is hydrogen or a linear or branched hydrocarbon radical having 6 to 30 carbon atoms and 0, 1, 2 or 3 double bonds,
B is hydrogen or a cation equivalent, and
n is on average a value of at least 0.1.

The invention further provides a process for preparing compounds of the general formula (I). The invention also provides the compounds of the general formula (I) obtainable by this process.

The invention further provides a cosmetic or pharmaceutical composition which comprises at least one compound of the general formula (I), as defined above and below.

The invention further provides the use of compounds of the general formula (I), as defined above and below, as surface-active substances, specifically as anionic surfactant for detergents and cleaners, cosmetic compositions, pharmaceutical compositions.

DESCRIPTION OF THE INVENTION

The compounds of the general formula (I) can be present in the form of mixtures or as pure compounds. For the uses according to the invention, mixtures of compounds of the general formula (I), as are obtainable e.g. by the preparation process described below, are generally suitable. The individual components of these mixtures can differ for example with respect to the degree of oligomerization n. If hydroxycarboxylic acids which have more than one carboxyl group and/or more than one alcoholic OH group are used for the preparation of the compounds of the general formula (I), then the individual components of these mixtures may also be structural isomers from the esterification reaction for their preparation. It is of course also possible to separate the reaction mixtures obtainable by the process according to the invention according to customary separation processes, e.g. by distillation or chromatography.

The average degree of oligomerization arises for the compounds according to the invention of the general formula (I) and of the general formula (I.1) by adding 1 to the value of the variables n.

Within the context of the invention, cation equivalent refers to a monovalent cation or the monovalent charge fraction of a polyvalent cation.

If B is a cation equivalent, then this is preferably selected from alkali metal cations, $NH_4^+$ and cations of the formula $HNE^1E^2E^{3+}$, where $E^1$, $E^2$ and $E^3$, independently of one another, are selected from hydrogen, linear and branched $C_1$-$C_6$-alkyl and linear and branched $C_1$-$C_4$-hydroxyalkyl, with the proviso that one of the radicals $E^1$, $E^2$ and $E^3$ is different from hydrogen. Preferably, the cation equivalent is selected from $Na^+$, $K^+$, $NH_4^+$, $Mg^{2+}/2$, $HN(CH_3)_3^+$, $HN(C_2H_5)_3^+$, $HN(C_2H_4OH)_3^+$, $H_2N(C_2H_4OH)_2^+$, etc.

Suitable linear or branched aliphatic hydrocarbon radicals having 1 to 30 carbon atoms and 0, 1, 2 or 3 double bonds are the corresponding $C_1$-$C_{30}$-alkyl radicals, $C_1$-$C_{30}$-alkenyl radicals, $C_1$-$C_{30}$-alkadienyl radicals and $C_1$-$C_{30}$-alkatrienyl radicals.

Preferably, at least one of the radicals $R^1$, $R^4$ or $R^5$ is a linear or branched aliphatic hydrocarbon radical having 1 to 30 carbon atoms and 0, 1, 2 or 3 double bonds. In particular, $R^1$, $R^4$ and $R^5$, independently of one another, are selected from methyl, ethyl, propyl, isopropyl, n-butyl, 2-butyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethyl-propyl, n-hexyl, 2-hexyl, 2-methylpentyl, 3-methylpentyl, 4-methylpentyl, 1,2-dimethyl-butyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2 ethylbutyl, 1-ethyl-2-methylpropyl, n-heptyl, 2-heptyl, 3-heptyl, 2-ethylpentyl, 1-propylbutyl, n-octyl, 2-ethylhexyl, 2-propylheptyl, n-nonyl, n-decyl, n-undecyl, n-dodecyl, n-tridecyl, n-tetra-decyl, n-pentadecyl, n-hexadecyl, n-heptadecyl, n-octadecyl, n-nonadecyl, arachinyl, behenyl, lignocerinyl, melissinyl, isotridecyl, isostearyl, oleyl, linoleyl, linolenyl, etc.

In a preferred embodiment, at least one of the radicals $R^1$, $R^4$ or $R^5$ is a linear or branched aliphatic hydrocarbon radical having 6 to 30 carbon atoms and 0, 1, 2 or 3 double bonds. Particularly preferably, $R^1$, $R^4$ and $R^5$, independently of one another, are selected from n-hexyl, 2-ethylhexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octa-decyl, n-nonadecyl, arachinyl, behenyl, lignocerinyl, melissinyl, isotridecyl, isostearyl, oleyl, linoleyl, linolenyl, and combinations thereof.

The radicals $R^1$, $R^4$ and $R^5$ can be derived from pure alcohols or from alcohol mixtures. Preferably, they are industrially available alcohols or alcohol mixtures. In one preferred embodiment, $R^1$, $R^4$ and $R^5$ are then independently of one another selected from predominantly linear alkyl, alkenyl, alkadienyl and alkatrienyl radicals, as occur in natural or synthetic fatty acids and the corresponding fatty alcohols.

In a further preferred embodiment, $R^1$, $R^4$ and $R^5$, independently of one another, are derived from fatty alcohols based on industrial alcohol mixtures. These include e.g. the alcohol mixtures produced during the hydrogenation of industrial methyl esters based on fats and oils. These further include the alcohol mixtures produced during the hydrogenation of aldehydes from the oxo synthesis (oxo alcohols) or the alcohol mixtures produced during the dimerization of unsaturated fatty alcohols.

Preferably, at least one of the radicals $R^1$, $R^4$ and $R^5$ is derived from linear saturated alcohols having 8 to 18 carbon atoms.

Particularly preferably, at least one of the radicals $R^1$, $R^4$ and $R^5$ is derived from a mixture of linear saturated $C_{12}$-/$C_{14}$-alcohols.

Furthermore preferably, at least one of the radicals $R^1$, $R^4$ and $R^5$ is derived from a $C_{16}$-/$C_{18}$-fatty alcohol mixture. Mixtures of cetyl (hexadecyl) and stearyl (octadecyl) are also referred to as cetearyl.

Preferably, in the compounds (I), the variables m1 and m2 have the same meaning.

The compounds of the general formula (I) are esters of oligohydroxycarboxylic acids. These can be derived from customary hydroxycarboxylic acids, such as lactic acid, glycolic acid, malic acid, tartaric acid, tartronic acid and mixtures thereof. Preferably, the compounds (I) are derived from lactic acid, glycolic acid, malic acid, tartaric acid or mixtures thereof. Particularly preferably, the compounds (I) are derived from lactic acid.

In the compounds of the general formula (I), n is preferably a value from 0.1 to 100, particularly preferably from 0.15 to 50, in particular from 0.2 to 20.

In the compounds of the general formula (I.1), n is preferably a value from 0.1 to 100, particularly preferably from 0.15 to 50, in particular from 0.2 to 20.

The invention further provides a process for preparing compounds of the general formula (I) in which
a) at least one hydroxycarboxylic acid of the general formula (I.A)

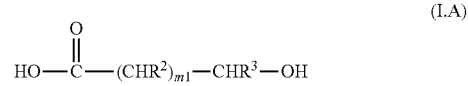

(I.A)

in which $R^2$, $R^3$ and m1 are as defined in any one of claims 1 to 8, is reacted in an esterification reaction, where the esterification takes place in the presence of at least one alcohol $R^1$—OH, where $R^1$ is as defined in any one of claims 1 to 8, or the product of the esterification of the hydroxycarboxylic acid(s) (I.A) is then reacted with at least one alcohol $R^1$—OH, b) the reaction product from step a) is reacted with a sulfating agent, and c) optionally the reaction product from step b) is at least partially neutralized with a base.

As regards suitable and preferred definitions of $R^1$, $R^2$, $R^3$, $R^4$, $R^5$ and m1, reference is made to the previous statements relating to these radicals and variables in their entirety.

Step a)

The esterification reaction in step a) can take place in several stages, in which case firstly at least one hydroxycarboxylic acid (I.A) is subjected to an esterification with oligomerization and then the resulting reaction mixture, optionally after a separation and/or purification, is reacted in a further esterification with at least one alcohol $R^1$—OH.

Preferably, the esterification reaction for preparing compounds of the general formula (I) takes place in the sense of a one-pot reaction in which at least one hydroxycarboxylic acid of the general formula (I.A) is subjected to an esterification in the presence of at least one alcohol $R^1$—OH.

The esterification reaction can take place in accordance with generally known processes, it being possible for the water of reaction that is formed to be removed e.g. by means of water-withdrawing agents, by extraction or by distillation.

Preferably, the water of reaction that is formed is removed by distillation. In a specific embodiment, the water of reaction that is formed is removed azeotropically. The reaction takes place in this connection in the presence of a solvent which forms an azeotropic mixture with water. Suitable solvents and entrainers are aliphatic and aromatic hydrocarbons, e.g. alkanes, such as n-hexane and n-heptane, cycloalkanes, such as cyclohexane and methylcyclohexane, aromatics, such as benzene, toluene and xylene isomers and so-called special-boiling-point spirits which have boiling points between 70 and 140° C. Particularly preferred entrainers are cyclohexane, methyl-cyclohexane and toluene. Suitable apparatuses for the azeotropic distillation with the elimination of the water of reaction and recycling of the solvent to the reaction vessel are known to the person skilled in the art. The solvent used can be removed from the reaction mixture after the esterification by means of customary methods, such as e.g. by distillation, optionally under reduced pressure.

If an alcohol $R^1$—OH with a sufficiently high boiling point is used for the esterification, e.g. a saturated or mono- or polyunsaturated fatty alcohol with at least 6 carbon atoms, then it is possible to dispense with the use of an entrainer during the distillative removal of the water of reaction.

The esterification temperature is generally in a range from about 50 to 250° C., particularly preferably from 70 to 200° C.

The esterification preferably takes place under atmospheric pressure or reduced pressure. For the distillative removal of the water of reaction, it is advantageous to carry out the esterification under reduced pressure. Preferably, the pressure during the esterification is in a range from 1 mbar to 1.1 bar, in particular 5 mbar to 1 bar, specifically 10 mbar to 900 mbar. This is true both for the single-stage variant of the esterification reaction described above and also for the two-stage variant.

The esterification can take place autocatalytically or in the presence of a catalyst. Suitable catalysts are strong acids, such as e.g. sulfuric acid, anhydrous hydrogen chloride, sulfonic acids, e.g. toluenesulfonic acid and methanesulfonic acid, and acidic ion exchangers. In the process according to the invention, sulfuric acid and p-toluene-sulfonic acid is preferably used as catalyst. The amount of esterification catalyst here is generally in a range from about 0.1 to 5% by weight, based on the total amount of components to be esterified.

Preferably, the esterification reaction takes place without the addition of an external solvent. This is true both for the single-stage variant of the esterification reaction described above and also the two-stage variant. However, it is alternatively possible to carry out the reaction according to the invention in the presence of an organic solvent that is inert under the reaction conditions, or a solvent mixture. Preference is given to aprotic solvents. The solvents used preferably have a boiling point of at least 120° C., in particular of at least 140° C. These include e.g. alkylene glycol dialkyl ethers such as ethylene glycol dimethyl ether, ethylene glycol diethyl ether, etc. Cyclohexanone (b.p.: 155° C.), N-methylpyrrolidone (b.p.: 204° C.), sulfolane (b.p.: 285° C.), nitrobenzene (b.p.: 210° C.), xylene (b.p.: 140° C.), for example, are likewise suitable.

The desired average degree of oligomerization (p=1+n) is established in the customary manner.

Thus, in the case of the two-stage variant of the esterification reaction described above, firstly an oligomeric hydroxycarboxylic acid with the desired average degree of oligomerization (p=1+n) can be prepared. For this purpose, the reaction mixture is left under water-withdrawing conditions for a period at the reaction temperature which suffices to achieve the desired average degree of oligomerization. Preferably, the reaction time is about 0.5 to about 24 hours, in particular about 1 to about 20 hours. The oligomeric hydroxycarboxylic acid obtained in this way is then reacted with at least one alcohol $R^1$—OH to give the end product. The molar ratio of alcohol component $R^1$—OH to oligomeric hydroxycarboxylic acid for this variant is about 1:1.

In the case of the single-stage variant of the esterification reaction described above, at least one hydroxycarboxylic acid of the general formula (I.A) is subjected to an esterification in the presence of at least one alcohol $R^1$—OH. According to this variant, the desired average degree of oligomerization n is established for example via the molar ratio of alcohol component $R^1$—OH to hydroxycarboxylic acid (I.A). For this variant, this is preferably 1:1.01 to 1:200, particularly preferably 1:1.1 to 1:100, in particular 1:1.15 to 1:50, specifically 1:1.2 to 1:20. Also in accordance with this variant, the reaction mixture is left under water-withdrawing conditions for a period at a reaction temperature which suffices to achieve compounds of the general formula (I) with the desired average degree of oligomerization. Preferably, the reaction time is about 0.5 to about 24 hours, in particular about 1 to about 20 hours.

Step b)

Sulfation reactions of surfactant alcohols are known to the person skilled in the art and are described e.g. in WO 93/24453, DE 40 03 096 A1 and in "Ullmann's Encyclopedia of Industrial Chemistry", 5$^{th}$ edition Vol. A25 (1994), pages 779-783 and in the literature references cited therein.

In principle, sulfur trioxide, sulfur trioxide complexes, solutions of sulfur trioxide in sulfuric acid ("oleum"), concentrated sulfuric acid, chlorosulfonic acid, sulfuryl chloride or else amidosulfonic acid can be used for sulfating the reaction product from step a).

Preferably, the sulfating agent used in step b) comprises $SO_3$ or consists of $SO_3$. Preferably, gaseous sulfur trioxide is used in a mixture with a gas that is inert under the reaction conditions of the sulfation. Preferred inert gases are nitrogen or air. Here, the sulfur trioxide is diluted with air or nitrogen and preferably used in the form of a gas mixture with ca. 1 to 10, in particular 3 to 6% by volume, sulfur trioxide.

The sulfation with $SO_3$ can be carried out continuously or discontinuously, but in particular in reactors which work in accordance with the falling-film principle.

Preferably, the reaction is carried out in the absence of solvents. However, customary solvents, such as e.g. orthoformic acid esters, dimethylformamide, 1,2-dichloroethane or tetrahydrofuran, can also be used for the sulfation of olefins, aromatics, alcohols and the like.

The sulfation with $SO_3$ is preferably carried out with a molar ratio of hydroxycarboxylic acid ester to $SO_3$ of 1:0.9 to 1:2.4. Particular preference is given here to a range from 1:1.0 to 1:1.3.

The sulfation with $SO_3$ is carried out for example at temperatures of from 10 to 98° C. In order, on the one hand, to ensure an adequately low viscosity of the feed materials and, on the other hand, to avoid too much thermal stress during the reaction, it is advisable to carry out the sulfation at a temperature in the range from 20 to 90° C.

If chlorosulfonic acid is used as sulfating reagent, then the corresponding alcohol component is preferably charged to a stirred apparatus under inert conditions and the chlorosulfonic acid is introduced. The molar ratio between alcohol component and chlorosulfonic acid is preferably 0.5:1 to 1:0.5, the ratio being particularly preferably 0.75:1 to 1:0.75. The molar ratio of alcohol component to chlorosulfonic acid is very particularly preferably about 1:1.

If sulfuric acid is used for the esterification, then a 75 to 100% strength by weight, preferably 85 to 98% strength by weight acid (so-called "concentrated sulfuric acid" or "sulfuric acid monohydrate") is expediently used. The esterification can be carried out in a solvent or diluent if it is desired for controlling the reaction, e.g. the evolution of heat. As a rule, the alcoholic reactant is initially introduced and the sulfating agent is gradually added with continuous mixing. If a complete esterification of the alcohol component is desired, the sulfating agent and the alcohol component are preferably used in the molar ratio of 1:1 to 1:1.5, particularly preferably from 1:1 to 1:1.2. The esterification is preferably carried out at temperatures of 20 to 90° C., particularly preferably 45 to 75° C. Optionally, it may be expedient to carry out the esterification in a low-boiling, water-immiscible solvent or diluent at its boiling point, in which case the water that is formed during the esterification is distilled off azeotropically.

Step c)

Bases for the neutralization which can be used are alkali metal bases such as sodium hydroxide solution, potassium hydroxide solution, sodium carbonate, sodium hydrogencarbonate, potassium carbonate or potassium hydrogencarbonate and alkaline earth metal bases such as calcium hydroxide, calcium oxide, magnesium hydroxide or magnesium carbonate, and amines. Suitable amines are e.g. $C_1$-$C_6$-alkylamines, preferably n-propylamine and n-butylamine, dialkylamines, preferably diethylpropylamine and dipropylmethylamine, trialkylamines, preferably triethylamine and triisopropylamine. Preference is given to amino alcohols, e.g. trialkanolamines, such as triethanolamine, alkyldialkanolamines, such as methyl- or ethyldiethanolamine, and dialkylalkanolamines, such as dimethylethanolamine, and also 2-amino-2-methyl-1-propanol. The neutralization of the acid groups can also be carried out with the help of mixtures of two or more bases. The base is particularly preferably selected from NaOH, KOH, 2-amino-2-methyl-1-propanol, triethylamine, diethylaminopropylamine, diethanolamine, triethanolamine, triisopropanolamine and mixtures thereof. The neutralization can take place partially or completely depending on the intended use. For a partial neutralization, e.g. 50 to less than 100% of the acid groups can be neutralized. Preference is given to complete neutralization.

The compounds of the general formula (I) and of the general formula (I.1) are advantageously suitable for use as anionic surfactants. They may be quite generally for example cosmetic compositions, pharmaceutical compositions, hygiene products, detergents and cleaners, coating compositions, compositions for the paper industry, compositions for the textile industry, etc.

The surfactants according to the invention can be used here as the sole surface-active substance. The compounds of the general formula (I) and of the general formula (I.1) are advantageously characterized by their good compatibility with further surfactants.

Surfactant-Containing Compositions

The compounds according to the invention of the general formula (I) or of the general formula (I.1) are particularly advantageously suitable for formulating surfactant-containing compositions. In particular, these are aqueous surfactant-containing compositions. The compounds (I) and (I.1) are characterized in such compositions by their good solubility in water, good compatibility with many of the active ingredients and auxiliaries used in cosmetics, a good foam forming capacity and good rheological behavior.

The surfactant-containing compositions according to the invention preferably have a total surfactant content of from 0.1 to 75% by weight, particularly preferably from 0.5 to 60% by weight, in particular from 1 to 50% by weight, based on the total weight of the surfactant-containing composition.

Suitable surfactants are anionic surfactants, nonionic surfactants, cationic surfactants, amphoteric surfactants and mixtures thereof that are different from the compounds (I).

Typical examples of anionic surfactants are soaps, alkylsulfonates, alkylbenzene-sulfonates, olefinsulfonates, alkyl ether sulfonates, glycerol ether sulfonates, methyl ester sulfonates, sulfo fatty acids, alkylsulfates, fatty alcohol ether sulfates, glycerol ether sulfates, fatty acid ether sulfates, hydroxy mixed ether sulfates, monoglyceride (ether) sulfates, fatty acid amide (ether) sulfates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, N-acylamino acids, such as, for example, acylglutamates and acylaspartates, and also acyllactylates, acyltartrates, alkyl oligoglucosidesulfates, alkyl glucose carboxylates, protein fatty acid condensates and alkyl (ether) phosphates.

Suitable soaps are e.g. alkali metal, alkaline earth metal and ammonium salts of fatty acids, such as potassium stearate.

Suitable olefinsulfonates are obtained e.g. by the addition reaction of $SO_3$ onto olefins of the formula $R^3$—CH=CH—$R^4$ and subsequent hydrolysis and neutralization, where $R^3$ and $R^4$, independently of one another, are H or alkyl radicals having 1 to 20 carbon atoms, with the proviso that $R^3$ and $R^4$ together have at least 6 and preferably 8 to 20, specifically 10 to 16, carbon atoms. As regards preparation and use, reference may be made to the review article "J. Am. Oil. Chem. Soc.", 55, 70 (1978). The olefinsulfonates can be in the form of alkali metal, alkaline earth metal, ammonium, alkylammonium, alkanolammonium or glucammonium salts. Preferably, the olefinsulfonates are in the form of sodium salts. The hydrolyzed alpha-olefinsulfonation product, i.e. the alpha-olefinsulfonates, are composed of ca. 60% by weight of alkanesulfonates and ca. 40% by weight of hydroxyalkanesulfonates; of this, about 80 to 85% by weight are monosulfonates and 15 to 20% by weight are disulfonates.

Preferred methyl ester sulfonates (MES) are obtained by sulfonation of the fatty acid methyl esters of vegetable or animal fats or oils. Preference is given to methyl ester sulfonates from vegetable fats and oils, e.g. from rapeseed oil, sunflower oil, soybean oil, palm oil, coconut fat, etc.

Preferred alkylsulfates are sulfates of fatty alcohols of the general formula $R^6$—O—$SO_3Y$, in which $R^6$ is a linear or branched, saturated or unsaturated hydrocarbon radical having 6 to 22 carbon atoms and Y is an alkali metal, the monovalent charge equivalent of an alkaline earth metal, ammonium, mono-, di-, tri- or tetralkylammonium, alkanolammonium or glucammonium. Suitable fatty alcohol sulfates are preferably obtained by sulfation of native fatty alcohols or synthetic oxoalcohols and subsequent neutralization. Typical examples of fatty alcohol sulfates are the sulfation products of caproic alcohol, caprylic alcohol, 2-ethylhexyl alcohol, capric alcohol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinyl alcohol, linolyl alcohol, linolenyl alcohol, behenyl alcohol and elaeostearyl alcohol, and the salts and mixtures thereof. Preferred salts of the fatty alcohol sulfates are the sodium and potassium salts, in particular the sodium salts. Preferred mixtures of the fatty alcohol sulfates are based on industrial alcohol mixtures which are formed e.g. during the high-pressure hydrogenation of industrial methyl esters based on fats and oils or during the hydrogenation of aldehydes from the oxo synthesis or during the dimerization of unsaturated fatty alcohols. Preference is given to using fatty alcohols and fatty alcohol mixtures having 12 to 18 carbon atoms and in particular 12 to 14 carbon atoms for the preparation of alkylsulfates. Typical examples thereof are industrial alcohol sulfates based on vegetable raw materials.

Preferred sarcosinates are sodium lauroyl sarcosinate or sodium stearoyl sarcosinate.

Preferred protein fatty acid condensates are wheat-based vegetable products.

Preferred alkylphosphates are alkyl esters of mono- and diphosphoric acid.

Suitable acylglutamates are compounds of the formula (I)

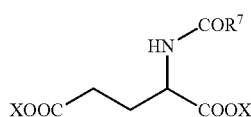

(I)

in which $COR^7$ is a linear or branched acyl radical having 6 to 22 carbon atoms and 0, 1, 2 or 3 double bonds and X is hydrogen, an alkali metal, the monovalent charge equivalent of an alkaline earth metal, ammonium, alkylammonium, alkanolammonium or glucammonium. The preparation of acylglutamates takes place for example by means of the Schotten-Baumann acylation of glutamic acid with fatty acids, fatty acid esters or fatty acid halides. Acylglutamates are commercially available for example from BASF SE, Clariant AG, Frankfurt/DE, or from Ajinomoto Co. Inc., Tokyo/JP. An overview of the preparation and properties of the acylglutamates can be found by M. Takehara et al. in J. Am. Oil Chem. Soc. 49 (1972) 143. Typical acylglutamates suitable as component b) are preferably derived from fatty acids having 6 to 22 and particularly preferably 12 to 18 carbon atoms. The mono- or dialkali metal salts of the acylglutamate, in particular, are used. These include e.g. (trade name of Ajinomoto, USA in brackets): sodium cocoyl glutamate (Amisoft CS-11), disodium cocoyl glutamate (Amisoft ECS-22SB), triethanolammonium cocoyl glutamate (Amisoft CT-12), triethanolammonium lauroyl glutamate (Amisoft LT-12), sodium myristoyl glutamate (Amisoft MS-11), sodium stearoyl glutamate (Amisoft HS-11 P) and mixtures thereof.

The nonionic surfactants include, for example:

fatty alcohol polyoxyalkylene esters, for example lauryl alcohol polyoxyethylene acetate, alkyl polyoxyalkylene ethers which are derived from low molecular weight $C_1$-$C_6$-alcohols or from $C_7$-$C_{30}$-fatty alcohols. Here, the ether component can be derived from ethylene oxide units, propylene oxide units, 1,2-butylene oxide units, 1,4-butylene oxide units and random copolymers and block copolymers thereof. These include specifically fatty alcohol alkoxylates and oxo alcohol alkoxylates, in particular of the type RO—$(R^8O)_r(R^9O)_sR^{10}$ where $R^8$ and $R^9$ independently of one another=$C_2H_4$, $C_3H_6$, $C_4H_8$ and $R^{10}$=H, or $C_1$-$C_{12}$-alkyl, R=$C_3$-$C_{30}$-alkyl or $C_6$-$C_{30}$-alkenyl, r and s independently of one another are 0 to 50, where both cannot be 0, such as isotridecyl alcohol and oleyl alcohol polyoxyethylene ethers, alkylarylalcohol polyoxyethylene ethers, e.g. octylphenol polyoxyethylene ether, alkoxylated animal and/or vegetable fats and/or oils, for example corn oil ethoxylates, castor oil ethoxylates, tallow fatty ethoxylates, glycerol esters, such as, for example glycerol monostearate, alkylphenol alkoxylates, such as, for example, ethoxylated isooctyl-, octyl- or nonylphenol, tributylphenol polyoxyethylene ether, fatty amine alkoxylates, fatty acid amide and fatty acid diethanolamide alkoxylates, in particular ethoxylates thereof, sugar surfactants, sorbitol esters, such as, for example, sorbitan fatty acid esters (sorbitan monooleate, sorbitan tristearate), polyoxyethylene sorbitan fatty acid esters, alkyl polyglycosides, N-alkylgluconamides, alkyl methylsulfoxides, alkyldimethylphosphine oxides, such as, for example, tetradecyldimethylphosphine oxide.

Suitable amphoteric surfactants are e.g. alkylbetaines, alkylamidopropylbetaines, alkyl-sulfobetaines, alkyl glycinates, alkyl carboxyglycinates, alkyl amphoacetates or -propionates, alkyl amphodiacetates or -dipropionates. For example, cocodimethylsulfopropylbetaine, laurylbetaine, cocamidopropylbetaine, sodium cocamphopropionate or tetradecyldimethylamine oxide can be used.

The cationic surfactants include, for example, quaternized ammonium compounds, in particular alkyltrimethylammonium and dialkyldimethylammonium halides and alkylsulfates, and pyridine and imidazoline derivatives, in particular alkylpyridinium halides. For example, behenyl or cetyltrimethylammonium chloride can be used. Also of suitability are so-called ester quats which are based on quaternary triethanol-methyl-ammonium or quaternary diethanol-dimethyl-ammonium compounds with long hydrocarbon chains in the form of fatty acid esters. These include, for example, bis (acyloxyethyl)hydroxyethylammonium methosulfate. Also of suitability is Dehyquart L 80 (INCI: Dicocoylethyl Hydroxyethylmonium Methosulfate (and) Propylene Glycol).

Cosmetic and Pharmaceutical Compositions

The compounds of the general formula (I) and of the general formula (I.1) are preferably suitable for formulating cosmetic and pharmaceutical products, specifically aqueous cosmetic and pharmaceutical products.

The invention further provides a cosmetic or pharmaceutical composition comprising
a) at least one compound of the general formula (I), as defined above,
b) at least one cosmetic or pharmaceutical active ingredient, and
c) optionally at least one cosmetic or pharmaceutical auxiliary that is different from components a) and b).

Preferably, at least one compound of the general formula (I.1) is used as component a).

Preferably, the component c) comprises at least one cosmetic or pharmaceutical carrier.

Preferably, the carrier component c) is selected from
i) water,
ii) water-miscible organic solvents, preferably $C_2$-$C_4$-alkanols, in particular ethanol,
iii) oils, fats, waxes,
iv) esters of $C_6$-$C_{30}$-monocarboxylic acids with mono-, di- or trihydric alcohols that are different from iii),
v) saturated acyclic and cyclic hydrocarbons,
vi) fatty acids,
vii) fatty alcohols,
viii) propellant gases,
and mixtures thereof.

Specifically suitable cosmetically compatible oil or fat components c) are described in Karl-Heinz Schrader, Grundlagen and Rezepturen der Kosmetika [Fundamentals and formulations of cosmetics], $2^{nd}$ edition, Verlag Huthig, Heidelberg, pp. 319-355, to which reference is hereby made.

The cosmetic compositions according to the invention may be skin cosmetic, hair cosmetic, dermatological, hygiene or pharmaceutical compositions. On account of their interface-active properties, the above-described compounds of the formula (I) and of the formula (I.1) are suitable particularly in compositions for cleaning the skin and/or the hair.

Preferably, the compositions according to the invention are in the form of an aqueous solution, a solid formulation (e.g. a soap bar or washing stick), a foam, an emulsion, a suspension, a lotion, a gel, a paste or a spray. If desired, liposomes or microspheres can also be used.

The cosmetic compositions according to the invention can additionally comprise cosmetic and/or dermatological active ingredients and effect substances and also auxiliaries. Preferably, the cosmetic compositions according to the invention comprise at least one compound of the formula (I) or of the formula (I.1), as defined above, at least one carrier C) as defined above and at least one constituent different therefrom which is preferably selected from cosmetic active ingredients, emulsifiers, surfactants, preservatives, perfume oils, additional thickeners, hair polymers, hair and skin conditioners, graft polymers, water-soluble or dispersible silicone-containing polymers, photoprotective agents, bleaches, gel formers, care agents, tinting agents, tanning agents, dyes, pigments, consistency regulators, humectants, refatting agents, collagen, protein hydrolyzates, lipids, antioxidants, defoamers, antistats, emollients and softeners.

In addition to the compounds of the formula (I) and of the formula (I.1), the cosmetic compositions can comprise at least one thickener. These include e.g. polysaccharides and organic sheet minerals such as Xanthan Gum® (Kelzan® from Kelco), Rhodopol® 23 (Rhone Poulenc) or Veegum® (R. T. Vanderbilt) or Attaclay® (Engelhardt). Suitable thickeners are also organic natural thickeners (agar agar, carrageenan, tragacanth, gum arabic, alginates, pectins, polyoses, guar flour, carob seed flour, starch, dextrins, gelatin, casein) and inorganic thickeners (polysilicic acids, clay minerals such as montmorillonites, zeolites, silicas). Further thickeners are polysaccharide gums, for example gum arabic, agar, alginates, carrageenans and their salts, guar, guaran, tragacanth, gellan, ramsan, dextran or xanthan and their derivatives, e.g. propoxylated guar, and their mixtures. Other polysaccharide thickeners are for example starches of highly diverse origin and starch derivatives, e.g. hydroxyethyl starch, starch phosphate esters or starch acetates, or carboxymethyl-cellulose or its sodium salt, methyl-, ethyl-, hydroxyethyl-, hydroxypropyl-, hydroxy-propyl-methyl- or hydroxyethyl-methyl-cellulose or cellulose acetate. Thickeners which can be used are also sheet silicates. These include for example the magnesium or sodium-magnesium sheet silicates from Solvay Alkali available under the trade name Laponite®, as well as the magnesium silicates from Sud-Chemie.

Suitable cosmetic and/or dermatological active ingredients are e.g. skin and hair pigmentation agents, tanning agents, bleaches, keratin-hardening substances, antimicrobial active ingredients, light filter active ingredients, repellant active ingredients, hyperemic substances, keratolytic and keratoplastic substances, antidandruff active ingredients, antiphlogistics, keratinizing substances, active ingredients that have an antioxidative effect and/or act as free-radical scavengers, skin-moisturizing or -humectant substances, refatting active ingredients, deodorizing active ingredients, sebostatic active ingredients, plant extracts, antierythematous or antiallergic active ingredients and mixtures thereof.

Artificially skin-tanning active ingredients which are suitable for tanning the skin without natural or artificial irradiation with UV rays are e.g. dihydroxyacetone, alloxan and walnut shell extract. Suitable keratin-hardening substances are generally active ingredients as are also used in antiperspirants, such as e.g. potassium aluminum sulfate, aluminum hydroxychloride, aluminum lactate, etc. Antimicrobial active ingredients are used in order to destroy microorganisms or to inhibit their growth and thus serve both as preservatives and as deodorizing substance which reduces the formation or the intensity of body odor. These include e.g. customary preservatives known to the person skilled in the art, such as p-hydroxybenzoic acid esters, imidazolidinylurea, formaldehyde, sorbic acid, benzoic acid, salicylic acid, etc. Deodorizing substances of this kind are e.g. zinc ricinoleate, triclosan, undecylenic acid alkylolamides, citric acid triethyl esters, chlorhexidin etc. Suitable light filter active ingredients are substances which absorb UV rays in the UV-B and/or UV-A region. Suitable UV filters are those mentioned above. Also of suitability are p-aminobenzoic acid esters, cinnamic acid esters, benzophenones, camphor derivatives, and pigments that stop UV rays, such as titanium dioxide, talc and zinc oxide. Suitable repellant active ingredients are compounds which are able to keep away or repel certain animals, in particular insects, from people. These include e.g. 2-ethyl-1,3-hexanediol, N,N-diethyl-m-toluamide etc. Suitable hyperemic substances, which stimulate blood flow through the skin, are e.g. essential oils, such as dwarf-pine, lavender, rosemary, juniper berry, horse chestnut extract, birch leaves extract, hay flower extract, ethyl acetate, camphor, menthol, peppermint oil, rosemary extract, eucalyptus oil, etc. Suitable keratolytic and keratoplastic substances are e.g. salicylic acid, calcium thioglycolate, thioglycolic acid and its salts, sulfur, etc. Suitable antidandruff active ingredients are e.g. sulfur, sulfur polyethylene glycol sorbitan monooleate, sulfur ricinol polyethoxylate, zinc pyrithione, aluminum pyrithione, etc. Suitable antiphologistics, which counteract skin irritations are, e.g. allantoin, bisabolol, dragosantol, chamomile extract, panthenol, etc.

The cosmetic compositions according to the invention can comprise at least one cosmetic or pharmaceutical polymer as cosmetic active ingredient (and also optionally as auxiliary). These include quite generally anionic, cationic, amphoteric and neutral polymers.

Examples of anionic polymers are copolymers of acrylic acid and acrylamide and salts thereof; sodium salts of polyhydroxycarboxylic acids, water-soluble or water-dispersible polyesters, polyurethanes, e.g. Luviset PUR® from BASF, and polyureas. Particularly suitable polymers are copolymers of t-butyl acrylate, ethyl acrylate, methacrylic acid (e.g. Luvimer® 100P), copolymers of ethyl acrylate and methacrylic acid (e.g. Luvimer® MAE), copolymers of N-tert-butylacrylamide, ethyl acrylate, acrylic acid (Ultrahold® 8, strong), copolymers of vinyl acetate, crotonic acid and optionally further vinyl esters (e.g. Luviset® grades), maleic anhydride copolymers, optionally reacted with alcohol, anionic polysiloxanes, e.g. carboxyfunctional, t-butyl acrylate, methacrylic acid (e.g. Luviskol® VBM), copolymers of acrylic acid and methacrylic acid with hydrophobic monomers, such as e.g. $C_4$-$C_{30}$-alkyl esters of (meth)acrylic acid, $C_4$-$C_{30}$-alkyl vinyl esters, $C_4$-$C_{10}$-alkyl vinyl ethers and hyaluronic acid. One example of an anionic polymer is also the methyl methacrylate/methacrylic acid/acrylic acid/urethane acrylate copolymer available under the name Luviset® Shape (INCI name: Polyacrylate-22). Examples of anionic polymers are also vinyl acetate/crotonic acid copolymers, as are commercially available for example under the names Resyn® (National Starch) and Gafset® (GAF), and vinylpyrrolidone/vinyl acrylate copolymers, available for example under the trade name Luviflex® (BASF). Further suitable polymers are vinylpyrrolidone/acrylate terpolymer available under the name Luviflex® VBM-35 (BASF) and sodium-sulfonate-containing polyamides or sodium-sulfonate-containing polyesters. Also of suitability are vinylpyrrolidone/ethyl methacrylate/meth-acrylic acid copolymers as sold by Stepan under the names Stepanhold-Extra and —R1 and the Carboset® grades from BF Goodrich.

Suitable cationic polymers are e.g. cationic polymers with the INCI name Polyquaternium, e.g. copolymers of vinylpyrrolidone/N-vinylimidazolium salts (Luviquat® FC, Luviquat® HM, Luviquat® MS, Luviset Clear®, Luviquat Supreme®, Luviquat® Care), copolymers of N-vinylpyrrolidone/dimethylaminoethyl methacrylate, quaternized with diethyl sulfate (Luviquat® PQ 11), copolymers of N-vinylcapro-lactam/N-vinylpyrrolidone/N-vinylimidazolium salts (Luviquat® Hold); cationic cellulose derivatives (Polyquaternium-4 and -10), acrylamide copolymers (Polyquaternium-7) and chitosan. Suitable cationic (quaternized) polymers are also Merquat® (polymer based on dimethyldiallylammonium chloride), Gafquat® (quaternary polymers which are formed by the reaction of polyvinylpyrrolidone with quaternary ammonium compounds), polymer JR (hydroxyethylcellulose with cationic groups) and plant-based cationic polymers, e.g. guar polymers, such as the Jaguar® grades from Rhodia.

Very particularly suitable polymers are neutral polymers, such as polyvinylpyrrolidones, copolymers of N-vinylpyrrolidone and vinyl acetate and/or vinyl propionate, polysiloxanes, polyvinylcaprolactam and other copolymers with N-vinylpyrrolidone, polyethyleneimines and salts thereof, polyvinylamines and salts thereof, cellulose derivatives, polyaspartic acid salts and derivatives. These include for example Luviflex® Swing (partially saponified copolymer of polyvinyl acetate and polyethylene glycol, BASF).

Suitable polymers are also nonionic, water-soluble or water-dispersible polymers or oligomers, such as polyvinylcaprolactam, e.g. Luviskol® Plus (BASF SE), or polyvinylpyrrolidone and copolymers thereof, in particular with vinyl esters, such as vinyl acetate, e.g. Luviskol® VA 37, VA 55, VA 64, VA 73 (BASF SE); polyamides, e.g. based on itaconic acid and aliphatic diamines, as are described e.g. in DE-A-43 33 238.

Suitable polymers are also amphoteric or zwitterionic polymers, such as the octyl-acrylamide/methyl methacrylate/tert-butylaminoethyl methacrylate/2-hydroxypropyl methacrylate copolymers obtainable under the names Amphomer® (National Starch), and also zwitterionic polymers, as are disclosed for example in the German patent applications DE 39 29 973, DE 21 50 557, DE 28 17 369 and DE 37 08 451. Acrylamidopropyltrimethylammonium chloride/acrylic acid or methacrylic acid copolymers and alkali metal and ammonium salts thereof are preferred zwitterionic polymers. Further suitable zwitterionic polymers are methacroylethyl-betaine/methacrylate copolymers which are commercially available under the name Amersette® (AMERCHOL), and copolymers of hydroxyethyl methacrylate, methyl methacrylate, N,N-dimethylaminoethyl methacrylate and acrylic acid (Jordapon®).

Suitable polymers are also nonionic, siloxane-containing, water-soluble or -dispersible polymers, e.g. polyethersiloxanes, such as Tegopren® (Goldschmidt) or Belsil® (Wacker).

In a specific embodiment, the compositions according to the invention comprise at least one polymer which acts as a thickener.

Suitable polymeric thickeners are, for example, optionally modified polymeric natural materials (carboxymethylcellulose and other cellulose ethers, hydroxyethyl- and -propylcellulose and the like), and synthetic polymeric thickeners (polyacrylic and polymethacrylic compounds, vinyl polymers, polycarboxylic acids, polyethers, polyamines, polyamides). These include the in part aforementioned polyacrylic and polymethacrylic compounds, for example the high molecular weight homopolymers of acrylic acid cross-linked with a polyalkenyl polyether, in particular an allyl ether of sucrose, pentaerythritol or propylene (INCI name: Carbomer). Such polyacrylic acids are available inter alia from BF Goodrich under the trade name Carbopol®, e.g. Carbopol 940 (molecular weight ca. 4 000 000), Carbopol 941 (molecular weight ca. 1 250 000) or Carbopol 934 (molecular weight ca. 3 000 000). They also include acrylic acid copolymers which are available for example from Rohm & Haas under the trade names Aculyn® and Acusol®, e.g. the anionic, non-associative polymers Aculyn 22, Aculyne 28, Aculyn 33 (crosslinked), Acusol 810, Acusol 823 and Acusol 830 (CAS 25852-37-3). Of specific suitability are also associative thickeners, e.g. based on modified polyurethanes (HEUR) or hydrophobically modified acrylic acid or methacrylic acid copolymers (HASE thickeners, High Alkali Swellable Emulsion).

According to one preferred embodiment, the compositions according to the invention are a skin cleaning composition.

Preferred skin cleaning compositions are soaps of liquid to gel-like consistency, such as transparent soaps, luxury soaps, deodorant soaps, cream soaps, baby soaps, skin protection soaps, abrasive soaps and syndets, pasty soaps, soft soaps and washing pastes, liquid washing, showering and bathing preparations, such as washing lotions, shower baths and gels, foam baths, oil baths and scrub preparations, shaving foams, shaving lotions and shaving creams.

Skin cleaning compositions preferably comprise at least compounds of the formula (I) and of the formula (I.1) in a fraction of about 0.001 to 70% by weight, preferably 0.01 to 50% by weight, very particularly preferably 0.1 to 30% by weight, based on the total weight of the composition.

According to a further preferred embodiment, the compositions according to the invention are a shower gel, a shampoo formulation or a bathing preparation.

Such formulations comprise at least one compound of the general formula (I) or (I.1) as base surfactant and optionally at least one amphoteric and/or nonionic surfactant as cosurfactant. Further suitable active ingredients and/or auxiliaries are generally selected from lipids, perfume oils, dyes, organic acids, preservatives, antioxidants, thickeners/gel formers, skin conditioners and humectants.

These formulations comprise preferably 2 to 50% by weight, preferably 5 to 40% by weight, particularly preferably 8 to 30% by weight, of surfactants, based on the total weight of the formulation.

All anionic, neutral, amphoteric or cationic surfactants that are customarily used in body cleaning compositions can additionally be used in the washing, showering and bathing preparations.

Suitable surfactants are those mentioned above.

Furthermore, the shower gel/shampoo formulations can additionally comprise thickeners, such as e.g. sodium chloride, PEG-55, propylene glycol oleate, PEG-120 methylglucose dioleate and others. Suitable commercially available further thickeners are e.g. Arlypon TT (INCI: PEG/PPG-120/10 Trimethylolpropane Trioleate (and) Laureth-2) and Arlypon F (INCI: Laureth-2). Furthermore, the shower gel/shampoo formulations can comprise preservatives, further active ingredients and auxiliaries and water.

The compounds according to the invention of the formula (I) and of the formula (I.1) are also advantageously suitable as surfactants for shampoo formulations, which can additionally comprise further customary surfactants.

In the shampoo formulations, customary conditioners can be used to achieve certain effects. These include, for example, the aforementioned cationic polymers with the INCI name Polyquaternium, in particular copolymers of vinylpyrrolidone/-N-vinylimidazolium salts (Luviquat® FC, Luviquat® HM, Luviquat® MS, Luviquat® Care), copolymers of N-vinylpyrrolidone/dimethylaminoethyl methacrylate, quaternized with diethyl sulfate (Luviquat® PQ 11), copolymers of N-vinylcaprolactam/N-vinyl-pyrrolidone/N-vinylimidazolium salts (Luviquat® Hold); cationic cellulose derivatives (polyquaternium-4 and -10), acrylamide copolymers (polyquaternium-7). Furthermore, protein hydrolyzates can be used, as can conditioning substances based on silicone compounds, for example polyalkylsiloxanes, polyarylsiloxanes, polyarylalkylsiloxanes, polyethersiloxanes or silicone resins. Further suitable silicone compounds are dimethicone copolyols (CTFA) and amino functional silicone compounds such as amodimethicones (CTFA). Furthermore, cationic guar derivatives such as guar hydroxypropyltrimonium chloride (INCI) can be used.

According to a further preferred embodiment, the compositions according to the invention are cosmetic compositions for the care and protection of the skin, nail care compositions or preparations for decorative cosmetics.

Moreover, the compounds of the formula (I) and of the formula (I.1) can be used in nose strips for pore cleansing, in antiacne compositions, repellents, shaving compositions, hair removal compositions, intimate care compositions, footcare compositions, and also in babycare.

Besides the compositions of the formula (I) and of the formula (I.1) and suitable carriers, the skin cosmetic preparations can also comprise further active ingredients and auxiliaries customary in skin cosmetics, as described above.

Preferred oil and fat components of the skin cosmetic and the dermatological compositions are mineral and synthetic oils, such as e.g. paraffins, silicone oils and aliphatic hydrocarbons having more than 8 carbon atoms, animal and vegetable oils, such as e.g. sunflower oil, coconut oil, avocado oil, olive oil, lanolin, or waxes, fatty acids, fatty acid esters, such as e.g. triglycerides of $C_6$-$C_{30}$-fatty acids, wax esters, such as e.g. jojoba oil, fatty alcohols, Vaseline, hydrogenated lanolin and acetylated lanolin, and mixtures thereof.

To establish certain properties such as e.g. improving the feel to the touch, the spreading behavior, the water resistance and/or the binding of active ingredients and auxiliaries, such as pigments, the skin cosmetic and dermatological preparations can additionally also comprise conditioning substances based on silicone compounds. Suitable silicone compounds are for example polyalkylsiloxanes, polyarylsiloxanes, polyarylalkylsiloxanes, polyethersiloxanes or silicone resins.

Cosmetic or dermatological preparations which comprise at least one compound of the formula (I) or of the formula (I.1) are produced by customary processes known to the person skilled in the art.

Preferably, the cosmetic and dermatological compositions are present in the form of emulsions, in particular as water-in-oil (W/O) or oil-in-water (O/W) emulsions. However, it is also possible to select other types of formulation, for example hydro dispersions, gels, oils, oleogels, multiple emulsions, for example in the form of W/O/W or O/W/O emulsions, anhydrous ointments or ointment bases, etc.

The preparation of emulsions takes place by known methods. Besides at least one compound of the formula (I) or of the formula (I.1), the emulsions generally comprise customary constituents, such as fatty alcohols, fatty acid esters and in particular fatty acid triglycerides, fatty acids, lanolin and derivatives thereof, natural or synthetic oils or waxes and emulsifiers in the presence of water. The selection of the emulsion-type-specific additives and the preparation of suitable emulsions is described for example in Schrader, Grundlagen and Rezepturen der Kosmetika [Fundamentals and formulations of cosmetics], Huthig Buch Verlag, Heidelberg, $2^{nd}$ edition, 1989, third part, to which reference is hereby expressly made.

Preferred fatty components which may be present in the fatty phase of the emulsions are: hydrocarbon oils, such as paraffin oil, purcellin oil, perhydrosqualene and solutions of microcrystalline waxes in these oils; animal or vegetable oils, such as sweet almond oil, avocado oil, calophylum oil, lanolin and derivatives thereof, castor oil, sesame oil, olive oil, jojoba oil, karite oil, hoplostethus oil; mineral oils, the distillation start-point of which under atmospheric pressure is ca. 250° C. and the distillation end-point of which is 410° C., such as e.g. vaseline oil; esters of saturated or unsaturated fatty acids, such as alkyl myristates, e.g. isopropyl, butyl or cetyl myristate, hexadecyl stearate, ethyl or isopropyl palmitate, octanoic or decanoic acid triglycerides and cetyl ricinoleate.

The fatty phase can also comprise silicone oils that are soluble in other oils, such as dimethylpolysiloxane, methylphenylpolysiloxane and the silicone glycol copolymer, fatty acids and fatty alcohols.

It is also possible to use waxes, such as e.g. carnauba wax, candelilla wax, beeswax, microcrystalline wax, ozokerite wax and Ca, Mg and Al oleates, myristates, linoleates and stearates.

Furthermore, an emulsion according to the invention can be present as an O/W emulsion. Such an emulsion usually comprises an oil phase, emulsifiers which stabilize the oil phase and the water phase, and an aqueous phase which is usually in thickened form. Suitable emulsifiers are preferably O/W emulsifiers, such as polyglycerol esters, sorbitan esters or partially esterified glycerides.

According to a further preferred embodiment, the compositions according to the invention are a hair treatment composition.

Hair treatment compositions according to the invention preferably comprise at least one compound of the general formula (I) or (I.1) in an amount in the range from about 0.1 to 30% by weight, preferably 0.5 to 20% by weight, based on the total weight of the composition.

The compounds according to the invention of the formula (I) and of the formula (I.1) are also suitable for styling gels. Gel formers which can be used are all gel formers that are customary in cosmetics. In this respect, reference is made to the conventional thickeners specified above.

The compounds according to the invention of the formula (I) and of the formula (I.1) are likewise suitable for producing pharmaceutical compositions.

Suitable pharmaceutical auxiliaries are the auxiliaries listed in the relevant pharmacopeia (e.g. DAB, Ph. Eur., BP, NF), and also other auxiliaries, the properties of which do not preclude a physiological application. Substances of this type are described for example also in Fiedler, H. P. Lexikon der Hilfsstoffe für Pharmazie, Kosmetik and angrenzende Gebiete [Lexicon of auxiliaries for pharmacy, cosmetics and related fields], 4$^{th}$ edition, Aulendorf: ECV-Editio-Kantor-Verlag, 1996.

Detergents and Cleaners

The compounds according to the invention of the formula (I) and of the formula (I.1) are also suitable for producing detergents or cleaners, e.g. for cleaning textile fabrics and/or hard surfaces. Cleaners of this type can be present in the form of a manual or machine dishwashing detergents, all-purpose cleaners for non-textile surfaces, e.g. made of metal, painted wood or plastic, or cleaners for ceramic articles, such as porcelain, slabs, tiles. Preferably, the detergents or cleaners according to the invention are in the form of a liquid textile detergent. If desired, these can also be formulated in paste form.

Examples of further formulations in which at least one compound of the general formula (I) or of the formula (I.1) as defined above can advantageously be used are e.g.

all-purpose cleaners, spray cleaners, manual dishwashing detergents for cleaning in the private, industrial and institutional sector;

humectants;

printing roll and printing plate cleaners in the printing industry;

paints and color formulations;

coatings, e.g. for paper;

adhesives;

formulations for spray applications, for example in inkjet inks;

leather treatment compositions;

compositions for treating metal, such as corrosion protection formulations;

cutting, abrading or boring auxiliaries and lubricants;

formulations in the textile industry, such as leveling agents or formulations for yarn cleaning;

flotation auxiliaries and foaming auxiliaries.

Such formulations usually comprise further ingredients such as surfactants, builders, fragrances and dyes, complexing agents, polymers and other ingredients. In general, the compounds according to the invention of the general formula (I) can be used in all areas in which a thickening interface-active effect is necessary. Furthermore, the compounds of the general formula (I) are suitable for improving the solubility of other components, e.g. of other surface-active components, such as of anionic surfactants. They thus also make a positive contribution to the formation of clear surfactant-containing solutions.

The invention is illustrated in more detail by reference to the following non-limiting examples.

EXAMPLES

Example 1

In a continuous falling-film reactor with jacket cooling and $SO_3$ gassing, 600 g of a technical-grade lauryl oligolactate (68% monoester) were reacted with sulfur trioxide at 40° C. The molar ratio was 1.2 mol of $SO_3$ per mole of lauryl oligolactate. The sulfur trioxide was driven out by heating from a corresponding amount of 65% strength by weight oleum, diluted with nitrogen to a concentration of 5% by volume and contacted with the lauryl lactate film via a nozzle. Then, together with 50% strength by weight sodium hydroxide solution, it was stirred into a 1% strength by weight solution of potassium dihydrogenphosphate and neutralized at a pH of 5.5 to 7.5.

| Analysis: | |
|---|---|
| Anionic surfactant content | 14.5% (MW = 374.4 g/mol) |
| Unsulfated: | 2.47% |
| Water according to Karl Fischer: | 83.9% |
| $Na_2SO_4$: | 1.7% |

Comparative Example

In a continuous falling-film reactor with jacket cooling and $SO_3$ gassing, 600 g of a lauryl lactate (87% monoester) were reacted with sulfur trioxide at 40° C. The molar ratio was 1.2 mol of $SO_3$ per mole of lauryl lactate. The sulfur trioxide was driven out by heating from a corresponding amount of 65% strength by weight oleum, diluted with nitrogen to a concentration of 5% by volume and contacted with the lauryl lactate film via a nozzle. Then, together with 50% strength by weight sodium hydroxide solution, it was stirred into a 1% strength by weight solution of potassium dihydrogenphosphate and neutralized at a pH of 5.5 to 7.5.

| Analysis | |
|---|---|
| Anionic surfactant: | 15.4% (MW = 368.5 g/mol) |
| Unsulfated: | 1.3% |
| Water according to Karl Fischer: | 82.8% |
| Na$_2$SO$_4$: | 1.72% |

Application Test:

The substance from example 1 and the comparison substance were adjusted to a concentration of 12% and increasing amounts of NaCl were added. The viscosity of the solutions was determined using a viscometer: Brookfield DII+pro at a measurement temperature of 22° C.

| amount NaCl [g/100 g] | Example 1 | Comparative example |
|---|---|---|
| | | Viscosity [mPa · s] |
| 0.5 | 280 | 120 |
| 1 | 1500 | 760 |
| 1.5 | 4800 | 3700 |
| 2 | 4700 | 4500 |

The example according to the invention exhibits a higher viscosity increase at lower NaCl concentrations.

Furthermore, the foaming behavior of the two substances was tested using a Sita rotor foam measuring instrument (1.0 g/l, 30° C., 1300 rpm; pH=5.5).

| Stirring time [s] | Example 1 | Comparative example |
|---|---|---|
| | | Foam volume [ml] |
| 0 | 0 | 0 |
| 10 | 231 | 237 |
| 20 | 392 | 400 |
| 30 | 532 | 539 |
| 40 | 765 | 765 |
| 50 | 829 | 828 |
| 60 | 851 | 849 |
| 70 | 860 | 857 |
| 80 | 866 | 861 |

The foaming behavior of both substances is identical within the scope of measurement accuracy.

The invention claimed is:

1. A compound of the general formula (I):

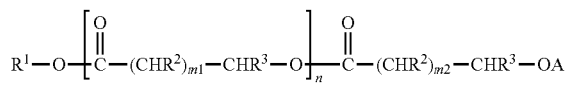

wherein:

R$^1$ is hydrogen or a linear or branched aliphatic hydrocarbon radical having 1 to 30 carbon atoms and 0, 1, 2 or 3 double bonds, the radicals R$^2$, independently of one another, are selected from hydrogen, methyl, ethyl, —OA, —COOR$^4$, —CH$_2$—OA and —CH$_2$—COOR$^4$, where the radicals R$^4$ are hydrogen or a linear or branched aliphatic hydrocarbon radical having 1 to 30 carbon atoms and 0, 1, 2 or 3 double bonds, the radicals R$^3$, independently of one another, are selected from hydrogen, methyl, ethyl, —OA, —COOR$^5$, —CH$_2$—OA and —CH$_2$—COOR$^5$, where the radicals R$^5$ are hydrogen or a linear or branched aliphatic hydrocarbon radical having 1 to 30 carbon atoms and 0, 1, 2 or 3 double bonds, A is H or —SO$_3$B, in which B is hydrogen or a cation equivalent, n is on average a value of at least 0.1, m1 and m2, independently of one another, are 0 or 1, with the proviso that at least one of the radicals A is —SO$_3$B, and with the proviso that at least one of the radicals R$^1$, R$^4$ or R$^5$ is a linear or branched aliphatic hydrocarbon radical having 1 to 30 carbon atoms and 0, 1, 2 or 3 double bonds.

2. The compound (I) according to claim 1, where m1 and m2 are the same.

3. The compound (I) according to claim 1, which is derived from lactic acid, glycolic acid, malic acid, tartaric acid or mixtures thereof.

4. The compound (I) according to claim 1, which is selected from a compound of the formula (I.1):

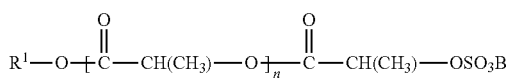

wherein:

R1 is hydrogen or a linear or branched hydrocarbon radical having 6 to 30 carbon atoms and 0, 1, 2 or 3 double bonds, B is hydrogen or a cation equivalent, and n is on average a value of at least 0.1.

5. The compound (I) according to claim 1, wherein n is a value from 0.1 to 100.

6. The compound (I) according to claim 1, wherein at least one of the radicals R$^1$, R$^4$ and R$^5$ is methyl, ethyl, n-propyl, isopropyl, n-butyl, isobutyl, sec-butyl, tert-butyl, n-pentyl, isoamyl, n-hexyl, 2-ethylhexyl, n-heptyl, n-octyl, n-nonyl, n-decyl, 2-propylheptyl, n-undecyl, n-dodecyl, n-tridecyl, n-tetradecyl, n-pentadecyl, n-hexadecyl, n-heptadecyl, n-octadecyl, n-nonadecyl, arachinyl, behenyl, lignocerinyl, melissinyl, isotridecyl, isostearyl, oleyl, linoleyl, linolenyl or a combination of at least two of these radicals.

7. The compound (I) according to claim 1, wherein at least one of the radicals R$^1$, R$^4$ and R$^5$ is derived from linear saturated alcohols having 8 to 18 carbon atoms.

8. The compound (I) according to claim 1, wherein at least one of the radicals R$^1$, R$^4$ and R$^5$ is derived from a mixture of linear saturated C$_{12}$-/C$_{14}$-alcohols.

9. A process for preparing compounds of general formula (I):

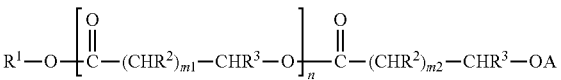

the process comprising:

a) reacting at least one hydroxycarboxylic acid of the general formula (I.A):

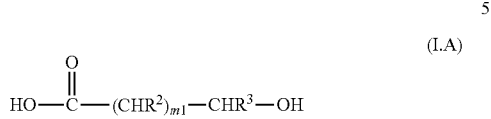
(I.A)

in an esterification reaction, where the esterification takes place in the presence of at least one alcohol $R^1$—OH or the product of the esterification of the hydroxycarboxylic acid(s) (I.A) is then reacted with at least one alcohol $R^1$—OH, wherein:

$R^1$ is hydrogen or a linear or branched aliphatic hydrocarbon radical having 1 to 30 carbon atoms and 0, 1, 2 or 3 double bonds, the radicals $R^2$, independently of one another, are selected from hydrogen, methyl, ethyl, —OA, —$COOR^4$, —$CH_2$—OA and —$CH_2$—$COOR^4$, where the radicals $R^4$ are hydrogen or a linear or branched aliphatic hydrocarbon radical having 1 to 30 carbon atoms and 0, 1, 2 or 3 double bonds, the radicals $R^3$, independently of one another, are selected from hydrogen, methyl, ethyl, —OA, —$COOR^5$, —$CH_2$—OA and —$CH_2$—$COOR^5$, where the radicals $R^5$ are hydrogen or a linear or branched aliphatic hydrocarbon radical having 1 to 30 carbon atoms and 0, 1, 2 or 3 double bonds, A is H or —$SO_3B$, in which B is hydrogen or a cation equivalent, n is on average a value of at least 0.1, m1 and m2, independently of one another, are 0 or 1, with the proviso that at least one of the radicals A is —$SO_3B$, and with the proviso that at least one of the radicals $R^1$, $R^4$ or $R^5$ is a linear or branched aliphatic hydrocarbon radical having 1 to 30 carbon atoms and 0, 1, 2 or 3 double bonds, b) reacting the reaction product from step a) with a sulfating agent, and c) optionally, at least partially neutralizing the reaction product from step b) with a base.

10. The process according to claim 9, where the sulfating agent of step b) comprises $SO_3$.

11. A cosmetic or pharmaceutical composition comprising:

a) at least one compound of the general formula (I) according to claim 1, b) at least one cosmetic or pharmaceutical active ingredient, and c) optionally at least one cosmetic or pharmaceutical auxiliary which is different from components a) and b).

12. The cosmetic composition according to claim 11 in the form of hair shampoos, shower gels, soaps, syndets, washing pastes, washing lotions, scrub preparations, foam baths, oil baths, shower baths, shaving foams, shaving lotions and shaving creams.

13. A detergent or cleaner comprising at least one compound of the general formula (I) according to claim 1.

14. The compound of the general formula (I) according to claim 1, which is effective as a surface-active substance.

15. The compound of the general formula (I) according to claim 1, which is effective as an anionic surfactant for cosmetic compositions, pharmaceutical compositions, detergents and cleaners.

16. The process according to claim 10, where the sulfating agent of step b) consists of $SO_3$.

17. The compound (I) according to claim 5, wherein n is a value from 0.15 to 50.

18. The compound (I) according to claim 17, wherein n is a value from 0.2 to 20.

* * * * *